United States Patent
Greff

(10) Patent No.: US 7,459,142 B2
(45) Date of Patent: Dec. 2, 2008

(54) HIGH VISCOSITY EMBOLIZING COMPOSITIONS COMPRISING PREPOLYMERS

(75) Inventor: Richard J. Greff, St. Petersburg Beach, FL (US)

(73) Assignee: Micro Therapeutics, Inc., Irvine, CA (US)

(*) Notice: Subject to any disclaimer, the term of this patent is extended or adjusted under 35 U.S.C. 154(b) by 0 days.

(21) Appl. No.: 10/162,653

(22) Filed: Jun. 6, 2002

(65) Prior Publication Data

US 2003/0228273 A1 Dec. 11, 2003

(51) Int. Cl.
*A61K 51/00* (2006.01)
*A61M 36/14* (2006.01)

(52) U.S. Cl. ............... 424/1.25; 424/1.11; 424/400; 424/422; 424/423; 424/1.37; 600/3; 600/4

(58) Field of Classification Search .......... 424/1.11, 424/1.25, 1.65, 9.1, 9.3, 1.29, 1.33, 1.37, 424/400, 422, 423; 600/3, 4
See application file for complete search history.

(56) References Cited

U.S. PATENT DOCUMENTS

| | | | |
|---|---|---|---|
| 3,527,224 A | 9/1970 | Rabinowitz | |
| 3,591,676 A | 7/1971 | Hawkins et al. | |
| 3,654,239 A | 4/1972 | McIntire et al. | |
| 4,038,345 A | 7/1977 | O'Sullivan et al. | |
| 5,580,568 A | 12/1996 | Greff et al. | |
| 5,667,767 A | 9/1997 | Greff et al. | |
| 5,695,480 A * | 12/1997 | Evans et al. | 604/264 |
| 5,702,361 A * | 12/1997 | Evans et al. | 604/508 |
| 5,795,922 A * | 8/1998 | Demian et al. | 523/117 |
| 5,888,546 A | 3/1999 | Ji et al. | |
| 6,015,541 A * | 1/2000 | Greff et al. | 424/1.25 |
| 6,103,254 A | 8/2000 | Wallace et al. | |
| 6,214,315 B1 * | 4/2001 | Greff et al. | 424/1.25 |
| 6,224,622 B1 * | 5/2001 | Kotzev | 606/214 |
| 6,241,719 B1 * | 6/2001 | Wallace et al. | 604/509 |
| 6,281,263 B1 * | 8/2001 | Evans et al. | 523/113 |
| 6,303,100 B1 * | 10/2001 | Ricci et al. | 424/1.29 |
| 6,333,020 B1 * | 12/2001 | Wallace et al. | 424/1.25 |
| 6,335,384 B1 * | 1/2002 | Evans et al. | 523/113 |
| 6,386,865 B1 * | 5/2002 | Suh et al. | 433/27 |
| 6,476,070 B2 * | 11/2002 | Krall et al. | 514/527 |
| 6,562,317 B2 * | 5/2003 | Greff et al. | 424/1.25 |
| 6,686,203 B2 * | 2/2004 | Calvo et al. | 436/63 |
| 6,759,028 B2 * | 7/2004 | Wallace et al. | 424/1.25 |
| 2003/0039696 A1 | 2/2003 | Porter | |

FOREIGN PATENT DOCUMENTS

| | | |
|---|---|---|
| EP | 1 208 855 A1 | 5/2002 |
| WO | WO 97/04657 | 2/1997 |
| WO | WO 98/04312 | 2/1998 |
| WO | WO 00/56380 | 9/2000 |
| WO | WO 00/71064 A1 | 11/2000 |

OTHER PUBLICATIONS

Tranbahuy et al (American Journal of Otolaryngology, vol. 15, No. 6, 1994, pp. 429-435).*
Mason et al (American Journal of Roentgenology, Dec. 2001, vol. 177, pp. 1359-1363).*
Picard et al (Journal of Neuroradiology, 1984, vol. 11, pp. 9-28).*
Summary Minutes of the Neurological Devices Advisory Panel Meeting, Open Session, May 11, 2000.
Mandai et al., "*Direct thrombosis of aneurysms with cellulose acetate polymer*", 77 J. Neurosurg. 497-500 (1992).
Kinugasa et al., "*Direct thrombosis of aneurysms with cellulose acetate polymer*," 77 J. Neurosurg. 501-507 (1992).
Amdur et al., Cassarett and Doull's Toxicology, Editors, Pergamon Press, New York, 661-664 (1975).
Kinugasa et al., "*Early treatment of subarachnoid hemmorrhage after preventing rerupture of an aneurysm*," 83 J Neurosurg. 34-41 (1995).
Kinugasa et al. "*Prophylactic Thrombosis to Prevent New Bleeding and to Delay Aneurysm Surgery*," 36(4) Neurosurg. 661-667 (1995).
Taki et al. "*Selection and combination of various endovascular techniques in the treatment of giant aneurysms*," 77 J. Neurosurg. 37-42 (1992).
Castaneda-Zuniga, et al., "*Interventional Radiology*," 1 Vascular Embolotherapy Part 1, 9-32, Williams & Wilkins (1992).

* cited by examiner

*Primary Examiner*—D. L Jones
(74) *Attorney, Agent, or Firm*—Foley & Lardner LLP

(57) ABSTRACT

Disclosed are novel high viscosity compositions for embolizing blood vessels which comprise a biocompatible prepolymer and a contrast agent, and optionally a thickening agent and/or a biocompatible solvent. Also disclosed are methods for embolizing a vascular site by injecting high viscosity prepolymer compositions into said site. The disclosed compositions and methods are particularly well suited for the treatment of aneurysms.

14 Claims, No Drawings

HIGH VISCOSITY EMBOLIZING COMPOSITIONS COMPRISING PREPOLYMERS

BACKGROUND OF THE INVENTION

1. Field of the Invention

This invention is directed to novel high viscosity compositions and for methods for embolizing blood vessels. The compositions of this invention are particularly useful for treating aneurysms.

In one embodiment, the compositions of this invention comprise a biocompatible prepolymer and a biocompatible contrast agent. Upon delivery to a mammalian vascular site, the viscosity of these compositions is at least about 150 centistokes at 40° C. Polymerization of these compositions in vivo results in the formation of a solid, coherent mass which embolizes the vascular site.

In another embodiment, the compositions of the invention are heated to at least 40° C. and mixed to form a uniform suspension, transferred to a delivery catheter having a proximal end and a distal end, wherein the distal end is positioned in the vascular site to be embolized, and the composition is injected into the vascular site in sufficient amounts to embolize said site.

Publications

The following publications are cited in this application as superscript numbers:

[1] Mandai et al., "*Direct Thrombosis of Aneurysms with Cellulose Acetate Polymer*", 77 J. NEUROSURG. 497-500 (1992).

[2] Kinugasa et al., "*Direct Thrombosis of Aneurysms with Cellulose Acetate Polymer,*" 77 J. NEUROSURG. 501-507 (1992).

[3] Amdur et al., Cassarett and Doull's TOXICOLOGY, Editors, Pergamon Press, New York, 661-664 (1975).

[4] Greff et al., U.S. Pat. No. 5,667,767, "*Novel Compositions for Use in Embolizing Blood Vessels,*" issued Sep. 16, 1997.

[5] Greff et al., U.S. Pat. No. 5,580,568, "*Cellulose Diacetate Compositions for Use in Embolizing Blood Vessels,*" issued Dec. 3, 1996.

[6] Kinugasa et al., "*Early Treatment of Subarachnoid Hemmorrhage After Preventing Rerupture of an Aneurysm,*" 83 J NEUROSURG. 34-41 (1995).

[7] Kinugasa et al. "*Prophylactic Thrombosis to Prevent New Bleeding and to Delay Aneurysm Surgery,*" 36 NEUROSURG. 661 (1995).

[8] Taki et al. "*Selection and Combination of Various Endovascular Techniques in the Treatment of Giant Aneurysms,*" 77 J. NEUROSURG. 37-42 (1992).

[9] Castaneda-Zuniga, et al., "*Interventional Radiology,*" 1 VASCULAR EMBOLOTHERAPY Part 1, 9-32, Williams & Wilkins (1992).

[10] Rabinowitz et al., U.S. Pat. No. 3,527,224, "*Method of Surgically Bonding Tissues Together,*" issued Sep. 8, 1970.

[11] Hawkins et al., U.S. Pat. No. 3,591,676, "*Surgical Adhesive Compositions,*" issued Jul. 6, 1971.

All of the above publications are herein incorporated by reference in their entirety to the same extent as if each individual publication was specifically and individually indicated to be incorporated herein by reference in its entirety.

2. State of the Art

Embolization of blood vessels is conducted for a variety of purposes, including the treatment of tumors, lesions (such as aneurysms), uncontrolled bleeding, and the like.

Embolization as part of the treatment of aneurysms is preferably accomplished via catheter techniques which permit the selective placement of the catheter in the aneurysmal sac. In this regard, recent advancements in catheter technology, as well as in angiography, now permit neuroendovascular intervention including treatment of what would otherwise have been inoperable lesions.

Embolizing compositions, or embolic compositions, known in the art prior to Applicant's invention typically included a biocompatible polymer, a biocompatible solvent, and a contrast agent, which allowed for visualization of the in vivo delivery of the composition via fluoroscopy.[1-8] The viscosity of the embolic compositions prior to Applicant's invention was typically low because only low-viscosity compositions could be delivered using conventional delivery technology.

Despite the many positive attributes of low-viscosity embolic compositions, certain problems did arise. For example, it was observed that low-viscosity embolic compositions migrated, solidified, and formed elongated, string-like masses distal from the point of ejection from the delivery catheter. This migration was observed to cause embolization not at the aneurysmal sac, but at arteries attendant to the aneurysmal sac. It was also observed that under high-flow conditions, the formed masses could fragment, which can lead to incapacitation or death of the patient.

This invention is based, in part, on the discovery that the formation of a solid, non-migratory mass having a substantially contiguous shape can be achieved by using embolic compositions comprising a biocompatible prepolymer and a biocompatible contrast agent wherein the composition has a viscosity of at least about 150 centistokes at 40° C.

SUMMARY OF THE INVENTION

This invention is directed, in part, to the novel and unexpected discovery that embolic compositions comprising a biocompatible prepolymer and a biocompatible contrast agent and having a viscosity of at least 150 centistokes at 40° C. provide for the in vivo formation of a solid, non-migratory mass which is substantially contiguous in shape. Accordingly, these compositions are useful for the in vivo treatment of aneurysms and high-flow fistulas and the like.

This invention is also directed to embolic compositions comprising a biocompatible prepolymer, a biocompatible contrast agent, a biocompatible solvent and/or thickening agent, such that upon delivery of the composition to a vascular site, a solid, coherent mass forms which embolizes said vascular site. The viscosity of these compositions is at least about 150 centistokes at 40° C. Such compositions are also useful for the in vivo treatment of aneurysms.

In these compositions, the viscosity preferably ranges from about 200 to about 5,000 centistokes at 40° C. More preferably, the viscosity of these compositions ranges from about 500 to about 5,000 centistokes at 40° C.

This invention is also directed to the novel and unexpected discovery that such embolic compositions may be heated and mixed to at least 40° C. to form a uniform suspension, transferred to a delivery catheter having a proximal end and a distal end, wherein the distal end of the delivery catheter is positioned at the vascular site to be embolized, and injected into said vascular site in sufficient amounts to embolize said vascular site. This method is particularly useful for the treatment of aneurysms.

Preferably, the embolic composition is delivered at temperatures above 40° C. In addition, the embolic composition delivered preferably has a viscosity in the range of about 200 to about 5,000 centistokes at 40° C.

DETAILED DESCRIPTION OF THE INVENTION

This invention is directed to novel high viscosity compositions for embolizing blood vessels comprising a biocompatible prepolymer and a biocompatible contrast agent and to methods for embolizing blood vessels using the same. This invention is particularly well suited for treating aneurysms.

Prior to discussing this invention in further detail, the following terms will first be defined:

The term "biocompatible" refers to a material which, in the amounts used, is substantially non-toxic.

"Biocompatible prepolymers" refers to materials which polymerize in situ to form a polymer and which, in the amounts employed, the formed products are substantially non-toxic, substantially non-reactable, and substantially non-immunogenic when used internally in the patient, and which are substantially insoluble in blood. Suitable biocompatible prepolymers include, by way of example, acrylates, cyanoacrylates,[9-11] ($C_1$-$C_6$) hydroxyalkyl ($C_1$-$C_6$) alkacrylate (e.g. hydroxyethyl methacrylate), epoxies, urethanes, silicones, partially reacted monomers or oligomers, and the like. The prepolymer can either be a monomer or a reactive oligomer.[11]

The term "biocompatible solvent" refers to a material which is liquid at least at body temperature of the mammal in which the biocompatible prepolymer is soluble and, in the amounts used, is substantially non-toxic. Suitable biocompatible solvents include, by way of example, ethanol, acetone, dimethylsulfoxide, analogues/homologues of dimethylsulfoxide, ethyl lactate, hexamethyldisiloxane, water, and the like. When aqueous mixtures are employed, the resulting polymer formed in vivo must be water insoluble. In one embodiment, the biocompatible contrast agent employed is a liquid such as Ethiodol® (iodinated poppy seed oil; Savage Laboratories, Melville, N.Y.), Lipiodol® (iodine addition product of ethyl esters of the fatty acids obtained from poppy seed oil), and the like which additionally acts as a solvent for the biocompatible prepolymer.

A "blood flow attenuating device" is a device that reduces the amount of blood flow at a particular location or locations and includes, by way of example, an inflatable microballoon.

The term "contrast agent" refers to radiopaque material capable of being monitored during injection into a mammalian subject by, for example, radiography. The contrast agent can either be water soluble or water insoluble. Examples of water soluble contrast agents include metrizamide, iopamidol, iothalamate sodium, iodomide sodium, and meglumine. Examples of water insoluble contrast agents include tantalum, tantalum oxide, tungsten, barium sulfate, gold, and platinum. Preferably, the contrast agent used in the instant invention is water insoluble (i.e., has a water solubility of less than 0.01 mg/ml at 20° C.) and has a preferred particle size of about 10 μm or less.

The term "embolize" refers to a process wherein a material is injected into a blood vessel which, in the case of, for example, an aneurysm, fills or plugs the aneurysmal sac and/or encourages clot formation so that blood flow into the aneurysm ceases. Embolization, in the case of a vascular site, refers to a process wherein a material is injected that fills the vascular site, thereby preventing blood flow therethrough. Embolization of blood vessels is important in preventing and/or controlling bleeding due to disease and/or lesions. Embolization may be used to ablate diseased tissue by terminating the diseased tissue's blood supply, e.g., tumor treatment.

The term "thickening agent" refers to any biocompatible material that increases the viscosity of the composition. Suitable thickening agents include high polymers such as polymethyl methacrylate or other preformed polymers soluble or dispersible in the composition, a suspending agent such as fumed silica, and the like. High polymers are those with molecular weights at or greater than 50,000, and preferably greater than 100,000.

Compositions

The prepolymer compositions employed in this invention are prepared by conventional methods well known in the art.

For example, these compositions can be prepared by employing sufficient amounts of the biocompatible prepolymer such that the composition has a viscosity of at least about 150 centistokes at 40° C. The viscosity of the composition is controlled by either the nature of the biocompatible prepolymer itself, by the presence of a thickening agent, or by the concentration of prepolymer in solvent, if solvent is employed. For example, the viscosity of the prepolymer composition can be increased by addition of the polymer thereto as described in U.S. Pat. Nos. 3,654,239 and 4,038,345, both of which are incorporated herein by reference in their entirety.

Sufficient amounts of a contrast agent are then added to achieve the effective concentration for the complete composition. Preferably, the contrast agent is a water insoluble contrast agent which is suspended in the prepolymer. When so employed, the water insoluble contrast agent preferably has a particle size of about 10 μm or less, and more preferably of from about 1 μm to about 5 μm. See, e.g., U.S. Pat. No. 5,695,480, which is incorporated herein by reference in its entirety.

When the prepolymer is liquid, the use of a biocompatible solvent is not absolutely necessary, but may be preferred to provide for an appropriate viscosity in the composition.

Methods

The compositions described above can then be employed in methods for the catheter assisted embolization of mammalian blood vessels. In such methods, a sufficient amount of the composition is introduced into the selected blood vessel via a catheter delivery means under fluoroscopy so that the blood vessel is embolized. The particular amount of embolic composition employed is dictated by the total volume of the vasculature to be embolized, the concentration of prepolymer in the composition, etc. Such factors are well within the skill of the art.

One particularly preferred method for catheter delivery of the embolic compositions of this invention to the selected vascular site is via a small diameter medical catheter connected to a threaded syringe. One example of a novel threaded syringe has a threaded plunger which is operable as a conventional syringe for aspiration of the embolic composition and then is used in a threaded manner for delivery of the embolic composition. The threaded syringe may also include a tactile or audible indication of delivery which allows the clinician to monitor delivery of the embolic composition without looking at the syringe. The catheter for delivery of the embolic compositions preferably has a burst strength of 100 psi or greater, and more preferably 200 psi or greater, and still more preferably 1000 psi or greater. In order to prevent catheter burst, the threaded syringe may be provided with a force release mechanism which prevents the clinician from applying pressures above the catheter burst strength. Suitable threaded syringes are disclosed in U.S. Provisional Patent Application Ser. No. 60/135,289, filed May 21, 1999, which application is incorporated herein by reference in its entirety. As an alternative delivery means to the threaded syringe, a syringe pump may be used.

Preferably, in order to enhance the in vivo delivery of a uniform suspension of this composition, the composition is mixed at a temperature of above 40° C. which ensures formation of a uniform suspension and then this heated composition is transferred while maintaining its temperature above room temperature, and preferably above 40° C., into the catheter for in vivo delivery.

Specifically, when the contrast agent is suspended in the prepolymer composition, a uniform suspension is achieved by mixing the compositions at a temperature above about 40° C., preferably from above about 40° C. to about 90° C., and more preferably from about 50° C. to about 70° C. The particular temperature employed should be sufficiently high to ensure adequate mixing of the composition.

In a particularly preferred embodiment, the composition is heated for a period of time from at least about 3 to about 20 minutes, and preferably from about 5-10 minutes, to facilitate formation of a uniform suspension. In some cases, the formation of a uniform suspension requires that the heated composition be placed in a suitable mixer, e.g., Vortex mixer, and is shaken until the suspension is homogeneous. In this case, after formation of the homogenous suspension via the mixer, the composition is preferably reheated to a temperature of from above about 40° C. to about 90° C., and preferably from about 50° C. to about 70° C. The specific temperature employed for heating is selected relative to the biocompatible prepolymer employed. Such selections are well within the skill of the art.

In either case, the heated composition is then transferred, preferably via a syringe, and delivered into the catheter under conditions wherein the temperature of the composition is above room temperature, and preferably above about 40° C. In one preferred embodiment, the conditions which effect such transfer are rapid transfer (e.g., transfer occurs within 2 minutes of heating cessation) of the composition to the catheter.

Surprisingly, the heated composition maintains both a uniform suspension and ease of delivery during catheter injection into a vascular site in a mammal and, when ejected at the distal end of the catheter, there is no evidence of trauma to this site. See, for example, U.S. patent application Ser. No. 09/574,963, entitled "Methods for Delivering In Vivo Uniform Dispersed Embolic Compositions of High Viscosity," which application is incorporated herein by reference in its entirety.

The particular catheter employed is not critical provided that polymeric catheter components are compatible with the embolic composition (i.e., the catheter components will not readily degrade in the embolic composition, the composition will not degrade the catheter, and the catheter components will not effect polymerization of the prepolymer). In this regard, it is preferred to use polyethylene in the catheter components because of its inertness in the presence of the embolic composition described herein. Other materials compatible with the embolic compositions can be readily determined by the skilled artisan and include, for example, other polyolefins, such as, polyethylene (80A-80D), polyester polyether block copolymer (30D-80D), Alcryn (chlorinated polyolefin) (60A-80A), Pebax (polyamide polyether block copolymer) (25D-70D); fluoropolymers, such as, PTFE (polytetrafluoroethylene, such as Teflon™), perfluoroalkoxy resin, fluorinated ethylene propylene polymers, ETFE, and SEBS (styrene ethylene butadiene styrene); silicones; interpenetrating networks of silicone; nylons (6/6, 6/10, and 6/12) and polyamide.

When delivered by catheter, preferred delivery techniques include those set forth in U.S. patent application Ser. No. 09/574,500, entitled "Methods For Embolizing Vascular Sites With an Embolizing Composition", which application is incorporated herein by reference in its entirety.

Utility

The compositions and methods described herein are useful in treating aneurysms. Accordingly, these compositions find use in human and other mammalian subjects requiring such treatment.

It is contemplated that these compositions can be employed as a carrier for a compatible pharmaceutically active compound wherein this compound is delivered in vivo for subsequent release. Such compounds include, by way of example only, antibiotics, anti-inflammatory agents, chemotherapeutic agents, anti-angiogenic agents, and the like.

The following examples are set forth to illustrate the claimed invention and are not to be construed as a limitation thereof. Unless otherwise stated, all percents are in weight percent of the total composition and all temperatures are in degrees Celsius.

EXAMPLES

In these examples and elsewhere, the following abbreviations have the following meanings:

| | |
|---|---|
| ° C = | degrees Celsius |
| cc = | cubic centimeters |
| cSt = | centistokes |
| DMSO = | dimethylsulfoxide |
| g = | gram |
| mL = | milliliter |
| mm = | millimeter |
| MW = | weight average molecular weight |
| ppm = | parts per million |
| μm = | micron |

Example 1

High Viscosity Cyanoacrylate Prepolymer Composition

Preparation of Prepolymer 100 g of n-butyl cyanoacrylate monomer (99+%) are placed in a 250 mL round bottom flask and heated with gently stirring at 60° C. until the viscosity increases to about 1000 cSt, about 5 hours. $SO_2$ gas is bubbled in to attain a concentration of 250 ppm of $SO_2$. The prepolymer is cooled and approximately 0.05% of hydroquinone is added to further prevent premature polymerization. The prepolymer is stored at −20° C.

The prepolymer may be sterilized by dry heat and stored at room temperature in sealed polyethylene containers or amber borosilicate vials.

Preparation of Embolic Composition

The stored prepolymer is brought to 55° C. 10 g of prepolymer are mixed with 5 g of micronized Tantalum powder in a 50 mL glass beaker. A 1 mL polypropylene syringe is used to further mix and withdraw the composition. The syringe is connected to the luer connection of the catheter and the composition injected. Cure time in contact with blood is within several seconds.

Additionally, a polymerization retardant/solvent such as iodinated poppyseed oil (e.g., Ethiodol®) may be added to the final mixture before injection in a 1:1 to 1:3 ratio of prepolymer to oil.

Example 2

High Viscosity Cyanoacrylate Prepolymer Composition

Preparation of Prepolymer 100 g of n-butyl cyanoacrylate monomer (99+%) are placed in a 250 mL round bottom flask. $SO_2$ gas is bubbled in to attain a concentration of 250 ppm of $SO_2$. Approximately 0.05% of hydroquinone is added to further prevent premature polymerization. 5 g of poly(methyl methacrylate), MW about 500,000, are added with stirring at room temperature. After dissolution of the polymer, the viscosity is about 750 cSt. The prepolymer is stored at −20° C.

The prepolymer may be sterilized by dry heat and stored at room temperature in sealed polyethylene containers or amber borosilicate vials.

Preparation of Embolic Composition

Same as in Example 1 above.

Example 3

High Viscosity Acrylate Prepolymer Composition

Preparation of Prepolymer

In a 250 mL flask 100 g of hydroxyethyl methacrylate and 2 g of ethylene glycol dimethacrylate are combined. 4 g of poly(hydroxyethyl methacrylate), MW about 600,000, are added at room temperature with stirring to bring the viscosity to about 1000 cSt. The prepolymer is stored in refrigeration.

The prepolymer may be sterilized by dry heat and stored at room temperature in sealed amber borosilicate vials.

Preparation of Embolic Composition 10 g of prepolymer are mixed with 5 g of micronized Tantalum powder in a 50 mL glass beaker. Immediately prior to use, a two-part polymerization initiator consisting of 5 mL of a 3% aqueous solution of hydrogen peroxide and 0.75 mL of a 5% aqueous solution of ferrous ammonium sulfate are added and mixed. A 1 mL polypropylene syringe is used to further mix and withdraw the composition. The syringe is connected to the luer connection of the catheter and the composition injected. Cure time is about 15 minutes.

Example 4

High Viscosity Silicone Prepolymer Composition

Preparation of Prepolymer 100 g of a vinyl terminated poly(dimethylsiloxane), molecular weight 17,000 and viscosity of 500 cSt, are mixed at room temperature with 4 g of a methylhydrosiloxane-dimethylsiloxane copolymer (molecular weight 2,000, 30 mole % methylhydrosiloxane). These materials are available from Gelest, Inc., Tullytown, Pa. The prepolymer may be sterilized by dry heat and stored at room temperature in sealed amber borosilicate vials.

Preparation of Embolic Composition 10 g of prepolymer are mixed with 5 g of micronized Tantalum powder in a 50 mL glass beaker. Immediately prior to use, 150-200 ppm of a platinum catalyst (3-3.5% platinum—divinyltetramethyldisiloxane complex) is added. A 1 mL polypropylene syringe is used to further mix and withdraw the composition. The syringe is connected to the luer connection of the catheter and the composition injected. Cure time is about 10 minutes.

In addition to the above, it is contemplated that materials other than prepolymers can be employed to effect in vivo embolization. For example, materials which condense in vivo to form a mass insoluble in the blood stream can be used, provided that the condensation product is one which effectively embolizes the vascular site. Such condensation products are, of course, distinct from prepolymers in that condensation does not require polymerization. One example of a condensation product suitable for use herein is the product formed by condensation of an alginate (a polysaccharide) with a suitable divalent cation, e.g., $Ca^{2+}$.

Specifically, alginates are salts of alginic acids, which is a polyuronide made up of a sequence for two hexuronic acids: beta-D mannuronic acid and alpha-L guluronic acid. Alginates are extracted from brown seaweeds and may be used as partially non-thermo reversible gelling and thickening agents.

Alginates are one of the most well-established hydrocolloids. Hydrocolloids serve primarily to thicken or gel water. This allows for viscosity control, stabilization of suspensions, emulsions, and foams, improved freeze/thaw stability, syneresis and boilout control, film formation, rheology control, etc.

Alginic acid is insoluble in water. When added to water, it swells. Alginates are made by neutralizing alginic acid to give soluble salt forms, including sodium, potassium, and ammonium salts. These monovalent salts are most commonly used as thickeners. Other materials which can be used in a manner similar to alginates are well known in the art.

From the foregoing description various modifications and changes in the above described compositions and methods will occur to those skilled in the art. All such modifications coming within the scope of the appended claims are intended to be included therein.

What is claimed is:

1. A method for embolizing a vascular site, said method comprising:
   (a) selecting an embolic composition comprising
   a cyanoacrylate prepolymer and/or partially reacted monomers and oligomers thereof;
   a biocompatible contrast agent, in an amount capable of being monitored during injection; and
   a thickening agent which is a polyacrylate polymer,
   wherein the viscosity of said composition prior to injection is at least about 150 centistokes at 40° C.;
   (b) transferring the embolic composition to a delivery catheter having a proximal end and a distal end, wherein the distal end of the delivery catheter is positioned at the vascular site to be embolized; and
   (c) injecting the embolic composition into said vascular site in sufficient amounts to embolize said vascular site.

2. The method according to claim 1, wherein the embolic composition further comprises a biocompatible solvent.

3. The method according to claim 1, wherein said composition has a viscosity of at least 200 centistokes at 40° C.

4. The method according to claim 1, wherein said composition has a viscosity of at least 500 centistokes at 40° C.

5. The method according to claim 1, wherein said composition has a viscosity of from at least 500 to 5,000 centistokes at 40° C.

6. The method according to claim 1, wherein said biocompatible contrast agent is a water insoluble contrast agent.

7. The method according to claim 6, wherein said water insoluble contrast agent is selected from the group consisting of tantalum, tantalum oxide, tungsten, barium sulfate, gold, and platinum.

8. The method according to claim 7, wherein said water insoluble contrast agent is tantalum.

9. The method according to claim 1, wherein said biocompatible solvent is selected from the group consisting of ethyl lactate, dimethylsulfoxide, ethanol, acetone, ETHIODOL®, LIPIODOL®, iodinated poppy seed oil, iodinated soy bean oil, water, and hexamethyldisiloxane.

10. The method according to claim 1, wherein said thickening agent is polymethyl methacrylate.

11. The method according to claim 1, comprising an additional step of (a') heating and mixing the embolic composition of step (a) to at least 40° C. to form a uniform suspension;

and wherein the material transferred in step (b) is the uniform suspension of step (a').

12. The method according to claim 11, wherein the composition transferred is maintained at a temperature above 40° C.

13. The method according to claim 1, wherein, prior to the embolic composition being injected, a blood flow attenuating device is inserted immediately upstream the ejection port of said catheter.

14. The method according to claim 13, wherein said blood flow attenuating device is an inflatable microballoon which permits both normal and attenuated blood flow depending upon whether the microballoon is deflated or inflated.

* * * * *